US011819388B2

(12) United States Patent
Martin

(10) Patent No.: US 11,819,388 B2
(45) Date of Patent: Nov. 21, 2023

(54) PRESSURE APPLYING DRESSING

(71) Applicant: BondTrue, LLC, Towson, MD (US)

(72) Inventor: David Zachary Martin, Towson, MD (US)

(73) Assignee: BONDTRUE, LLC, Towson, MD (US)

( * ) Notice: Subject to any disclaimer, the term of this patent is extended or adjusted under 35 U.S.C. 154(b) by 35 days.

(21) Appl. No.: 17/679,155

(22) Filed: Feb. 24, 2022

(65) Prior Publication Data

US 2022/0175584 A1 Jun. 9, 2022

Related U.S. Application Data

(62) Division of application No. 16/506,067, filed on Jul. 9, 2019, now abandoned.

(60) Provisional application No. 62/696,083, filed on Jul. 10, 2018.

(51) Int. Cl.
*A61F 13/02* (2006.01)
*A61F 13/00* (2006.01)

(52) U.S. Cl.
CPC ........ *A61F 13/024* (2013.01); *A61F 13/0266* (2013.01); *A61F 2013/0028* (2013.01); *A61F 2013/00148* (2013.01)

(58) Field of Classification Search
CPC ........ A61F 13/00; A61F 13/02; A61F 13/023; A61F 13/0236; A61F 13/00021; A61F 13/024; A61F 13/0266; A61F 13/00034; A61F 13/00038; A61F 2013/00148; A61F 2013/0028; A61F 2013/00119; A61F 2013/00123; A61F 2013/00089; A61F 2013/00131; A61K 9/70; A61K 9/7007; A61K 47/6953; A61L 15/00; A61L 26/00; A61M 35/00
USPC .......... 602/41, 52, 53, 54, 58; 128/887–894; 604/304–308; 424/400, 443, 447–449
See application file for complete search history.

(56) References Cited

U.S. PATENT DOCUMENTS

| | | | |
|---|---|---|---|
| 2,421,193 A | 5/1947 | Gardner | |
| 9,539,148 B2 * | 1/2017 | Spinelli | ............... A61F 13/0243 |
| 2012/0226214 A1 * | 9/2012 | Gurtner | ............... A61F 13/0226 |
| | | | 602/53 |
| 2013/0110026 A1 * | 5/2013 | Jackson | ............ A61F 13/00034 |
| | | | 602/53 |

* cited by examiner

*Primary Examiner* — Caitlin A Carreiro
(74) *Attorney, Agent, or Firm* — TAROLLI, SUNDHEIM, COVELL & TUMMINO L.L.P.

(57) ABSTRACT

A dressing for applying pressure to a patient target site is provided. The dressing includes an elastic spacer longitudinally extending between first and second substrates. The elastic spacer is configured to be selectively moved between the first length and a second length. The second length is longer than the first length. A triggering element, when present, selectively maintains the elastic spacer at the second length and selectively prevents the elastic spacer from moving toward the first length. Portions of the triggering element are sequentially removable such that as each portion of the triggering element is removed, the elastic spacer sequentially moves from the second length toward the first length. The sequential movement of the elastic spacer from the second length toward the first length responsively urges the first and second substrates longitudinally toward one another to apply a predetermined amount of longitudinal force to the patient target site.

12 Claims, 10 Drawing Sheets

PRESSURE APPLYING DRESSING

RELATED APPLICATION

This application is a divisional application of and claims priority from U.S. application Ser. No. 16/506,067, filed 9 Jul. 2019, which claims priority from U.S. Provisional Application No. 62/696,083, filed 10 Jul. 2018, the subject matter of each of which is incorporated herein by reference in its entirety.

TECHNICAL FIELD

This disclosure relates to an apparatus and method for use of a dressing for applying pressure to a patient target site.

BACKGROUND

In certain situations, dressings are used to apply a predetermined amount of pressure to a patient's skin, to a wound, to close a wound, to keep a wound closed, to remove tension from a wound, to redistribute tension away from a wound, to evert a wound, and/or for any other purpose. In some situations, it might be desirable to increase the amount of pressure or force provided by a dressing over time without having to apply a new dressing. It might also be desirable for a user to be able to immediately adjust the pressure to a wound at the time of an initial application of a dressing.

SUMMARY

In an aspect, a dressing for applying pressure to a patient target site is provided. The dressing includes longitudinally spaced first and second substrates each having a first surface and an oppositely facing second surface. The first surface of each of the first and the second substrates has an attachment member for attaching the dressing to the patient target site. An elastic spacer longitudinally extends between the first and the second substrates. The elastic spacer is biased to a first length. The elastic spacer is configured to be selectively moved between the first length and a second length. The second length is longer than the first length. A triggering element is removably joined to at least one of the second surface of the first substrate, the second surface of the second substrate, and the elastic spacer. The triggering element, when present, selectively maintains the elastic spacer at the second length and selectively prevents the elastic spacer from moving toward the first length. Portions of the triggering element are sequentially removable from at least one of the second surface of the first substrate, the second surface of the second substrate, and the elastic spacer such that as each portion of the triggering element is removed, the elastic spacer sequentially moves from the second length toward the first length. The sequential movement of the elastic spacer from the second length toward the first length responsively urges the first and second substrates longitudinally toward one another to apply a predetermined amount of longitudinal force to the patient target site.

In an aspect, a method for applying pressure to a patient target site is provided. A dressing having an elastic spacer longitudinally extending between longitudinally spaced first and second substrates is provided. The elastic spacer is adjusted from a first length to a second length. The second length is longer than the first length. A triggering element is joined to at least one of a second surface of the first substrate, a second surface of the second substrate, and the elastic spacer to selectively maintain the elastic spacer at the second length and, with the triggering element, selectively prevent the elastic spacer from achieving the first length. The first substrate is attached to a first side of the patient target site. The second substrate is attached to a second side of the patient target site opposite the first side, to longitudinally span the patient target site with the elastic spacer. Portions of the triggering element are sequentially removed. The sequential removal of portions of the triggering element causes the elastic spacer to sequentially move from the second length to the first length. The sequential movement of the elastic spacer from the second length to the first length responsively urges the first and second substrates longitudinally toward one another to apply a predetermined amount of longitudinal force to the patient target site.

In an aspect, a dressing for applying pressure to a patient target site is provided. The dressing includes longitudinally spaced first and second substrates each having a first surface and an oppositely facing second surface. The first surface of each of the first and the second substrates has an attachment member for attaching the dressing to the patient target site. An elastic spacer longitudinally extends between the first and the second substrates. The elastic spacer is biased to a first length. The elastic spacer is configured to be selectively moved between the first length and a second length. The second length is longer than the first length. A triggering element is laterally removably inserted into a corresponding expandable cavity of the elastic spacer. The triggering element, when present, selectively maintains the elastic spacer at the second length and selectively prevents the elastic spacer from moving toward the first length. The triggering element is removable from the corresponding expandable cavity of the elastic spacer such that as the triggering element is removed, the elastic spacer moves from the second length toward the first length.

BRIEF DESCRIPTION OF THE DRAWINGS

For a better understanding, reference may be made to the accompanying drawings, in which.

DESCRIPTION OF EMBODIMENTS

Figure 1:
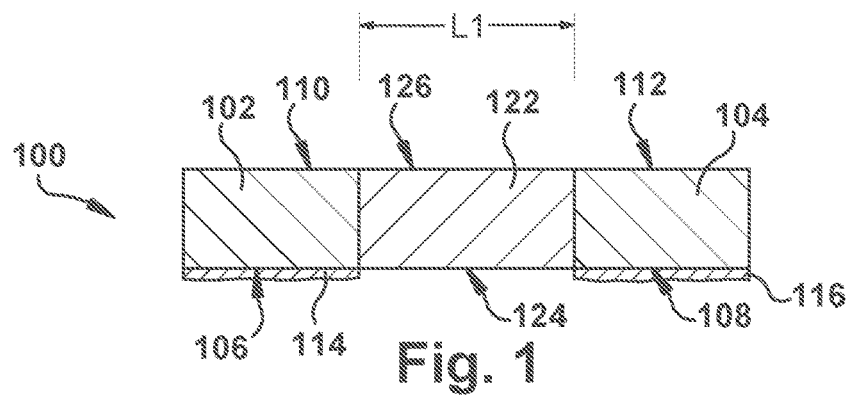
FIG. 1 is a cross-sectional view of a dressing for applying pressure to a patient target site according to one aspect of the present invention.

Unless defined otherwise, all technical and scientific terms used herein have the same meaning as is commonly understood by one of ordinary skill in the art to which the present disclosure pertains.

As used herein, the term "patient" can refer to any organism including, but not limited to, human beings, pigs, rats, mice, dogs, goats, sheep, horses, monkeys, apes, rabbits, cattle, reptiles, farm animals, livestock, etc.

As used herein, the term "user" can be used interchangeably to refer to an individual who prepares for, assists, and/or performs a procedure.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" can be interpreted to include X and Y.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "connected" to, "contacting," etc., another element, it can be directly on, attached to, connected to or contacting the other element or intervening elements may also be present. In contrast, when an element is referred to as being, for example, "directly contacting" another element, there are no intervening elements present.

Spatially relative terms may be used herein for ease of description to describe one element or feature's relationship to another element(s) or feature(s) as illustrated in the Figures. It will be understood that the spatially relative terms can encompass different orientations of a device in use or operation, in addition to the orientation depicted in the Figures.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

A dressing 100 for applying pressure to a patient target site is provided. As shown in FIGS. 1-4, the dressing 100 may include longitudinally spaced first and second substrates 102, 104 each having a first surface 106, 108 and an oppositely facing second surface 110, 112. The term "longitudinal" is used herein to indicate a substantially horizontal direction, in the orientation of FIG. 1. The first surface 106, 108 of each of the first and the second substrates 102, 104 may have an attachment member 114, 116 for attaching the dressing 100 to the patient target site T. As shown in FIG. 2, at least one removable cover 218 (shown here as removable covers 218a, 218b) may at least partially cover each of the attachment members 114, 116 of the first and second substrates 102, 104 prior to use.

Figure 2:
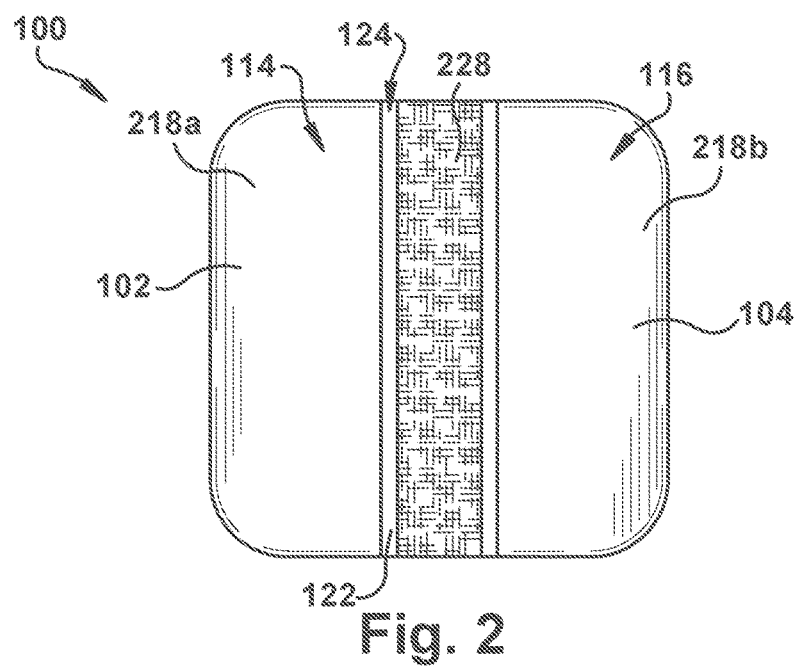
FIG. 2 is a bottom view of an element of FIG. 1, including an element in a first example configuration.
Figure 3:
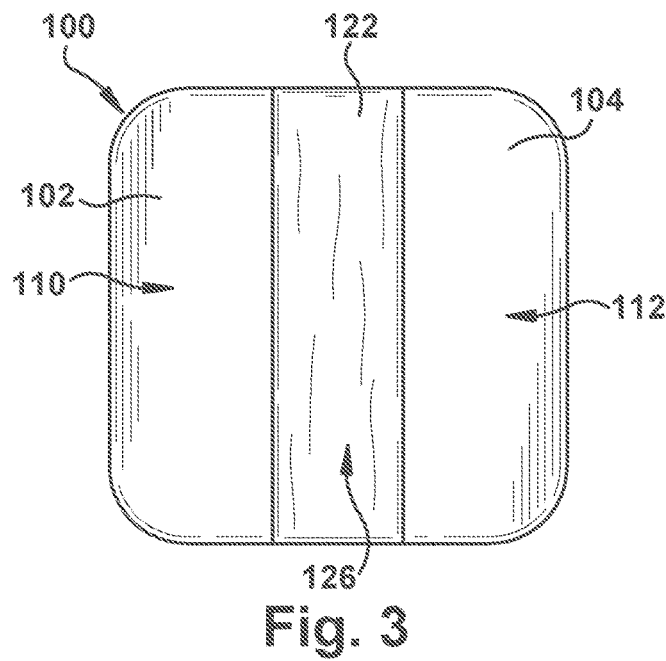
FIG. 3 is a top view of an element of FIG. 1.
Figure 4:
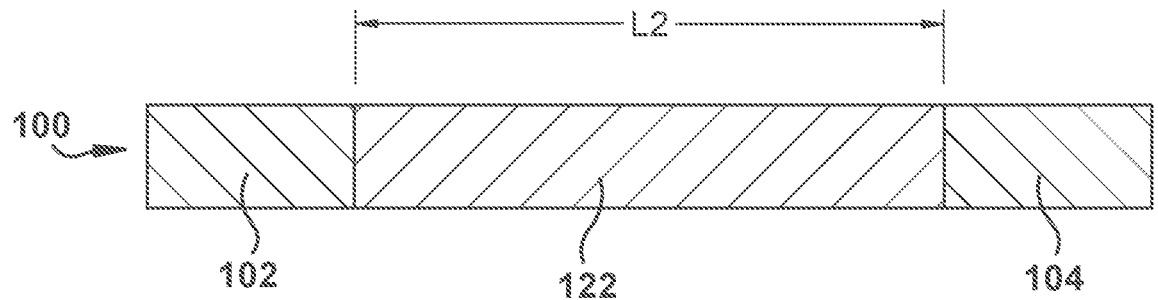
FIG. 4 is a cross-sectional view of an element of FIG. 1.

As shown in FIGS. 1-4, an elastic spacer 122 longitudinally extends between the first and the second substrates 102, 104. The elastic spacer 122 has a first surface 124 and an oppositely facing second surface 126. The elastic spacer 122 may be biased to a first elastic spacer length L1 (FIG. 1). The elastic spacer 122 is configured to be selectively moved between the first elastic spacer length L1 (FIG. 1) and a second elastic spacer length L2 (FIG. 4). The second elastic spacer length L2 is longer than the first elastic spacer length L1. Although the elastic spacer 122 has been described as being moved between the first and second elastic spacer lengths L1, L2, the elastic spacer 122 might be configured to be moved to any intermediate elastic spacer length between the first and second elastic spacer lengths L1, L2.

As shown in FIG. 2, the first surface 124 of the elastic spacer 122 may have at least one interfacing element 228 for contacting a target patient site T. The at least one interfacing element 226 might be at least one of gauze; perforated plastic film dressing, such as that available under the name Telfa™ from Cardinal Health of Dublin, Ohio; alginate; any desired biocompatible material; any material desirable for being placed on an open wound; or any combination thereof. When the elastic spacer 122 has the first elastic spacer length L1, the at least one interfacing element 228 may continuously span between the first and second substrates 102, 104. Portions of the at least one interfacing element 228 might at least partially overlap other portions of the at least one interfacing element 228 when the elastic spacer 122 has at least one of the first elastic spacer length L1 and the second elastic spacer length L2.

Figure 5:
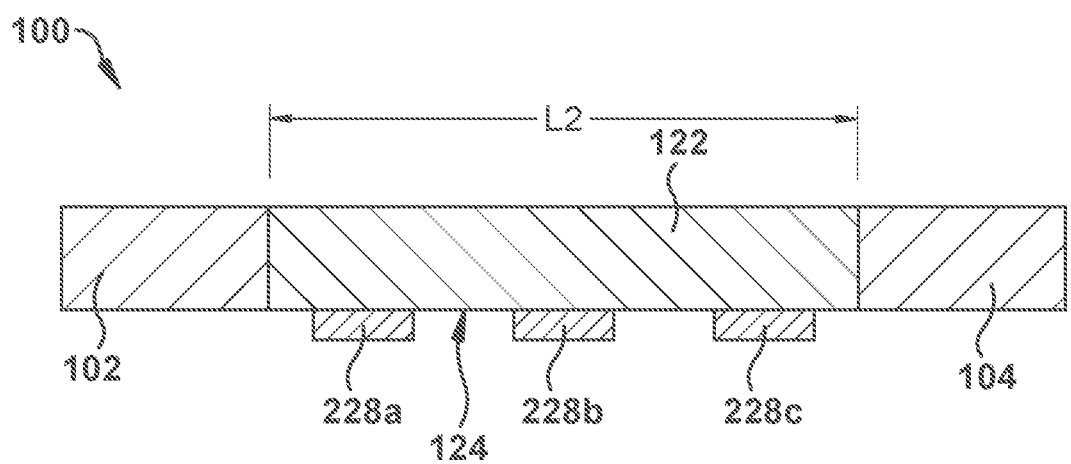
FIGS. 5-6 illustrate an example sequence of operation of a portion of the aspect of FIG. 1, including an element in a second example configuration.
Figure 6:
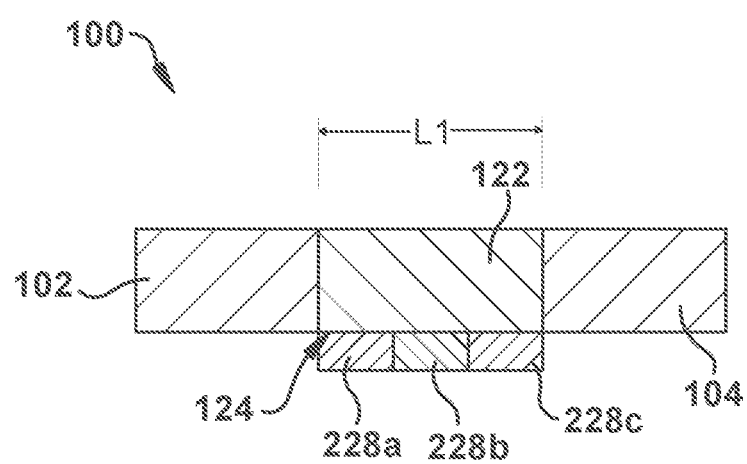

As shown in FIG. 5, the at least one interfacing element 228 might be at least two interfacing elements 228 (shown here as interfacing elements 228a, 228b, 228c). A chosen one of the at least two interfacing elements 228a, 228b, 228c might be longitudinally parallel with another of the at least two interfacing elements 228a, 228b, 228c. As shown in FIG. 5, the at least two interfacing elements 228a, 228b, 228c are longitudinally spaced apart from one another when the elastic spacer 122 has the second length L2. As shown in FIG. 6, when the elastic spacer 122 has the first length L1, the chosen one of the at least two interfacing elements 228a, 228b, 228c might directly longitudinally contact another of the at least two interfacing elements 228a, 228b, 228c so that the at least two interfacing elements 228a, 228b, 228c, as a whole, continuously span between the first and second substrates 102, 104. Instead or additionally to a chosen one of the at least two interfacing elements 228a, 228b, 228c directly longitudinally contacting another of the at least two interfacing elements 228a, 228b, 228c when the elastic spacer 122 has the first length L1, portions of the at least two interfacing elements 228a, 228b, 228c might at least partially overlap other portions of the at least two interfacing elements 228a, 228b, 228c when the elastic spacer 122 has the first elastic spacer length L1 so that the at least two interfacing elements 228a, 228b, 228c, as a whole, continuously span between the first and second substrates 102, 104 when the elastic spacer 122 has the first elastic spacer length L1.

The dressing 100 may include at least one triggering element 730. The at least one triggering element 730 might be removably attached to at least one of the second surface 110 of the first substrate 102, the second surface 112 of the second substrate 104, and the second surface 126 of the elastic spacer 122. The attachment between the triggering element 730 and at least one of the second surface 110 of the first substrate 102, the second surface 112 of the second substrate 104, and the second surface 126 of the elastic spacer 122 might be an adhesive attachment, a magnetic attachment, a hook and loop attachment, a button attachment, any other appropriate attachment, or any combination thereof. The triggering element 730, when present, selectively maintains the elastic spacer 122 at a length longer than the first elastic spacer length L1, such as the second length L2, and selectively prevents the elastic spacer 122 from moving toward the first length L1.

Figure 7:
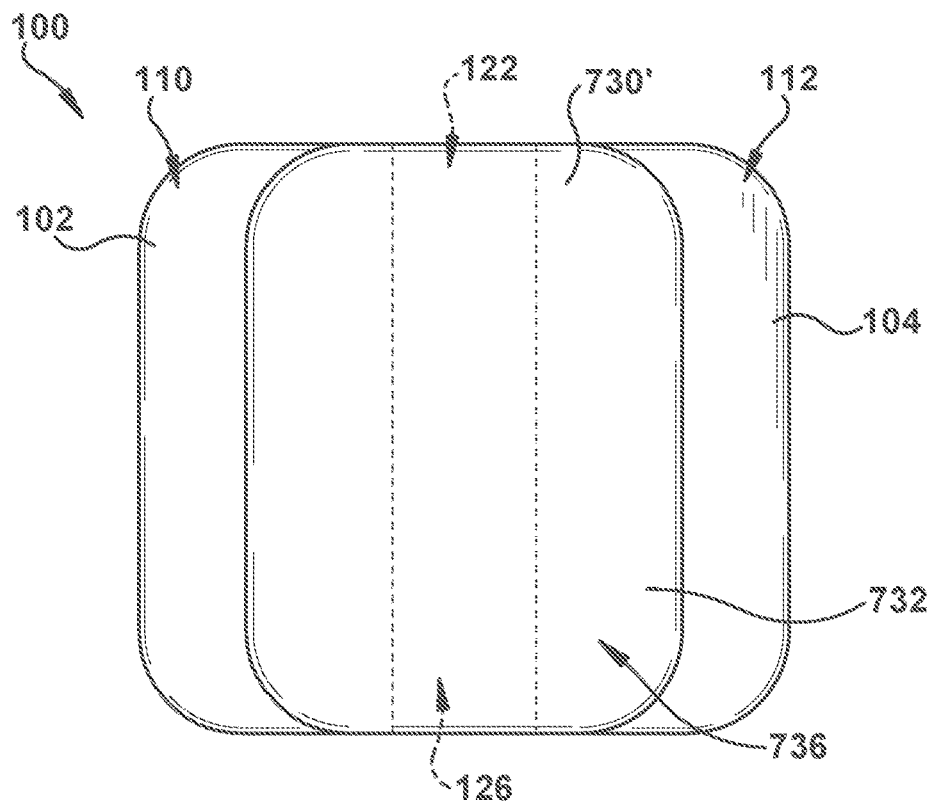
FIG. 7 is a top view of an element of the aspect of FIG. 1.
Figure 8:
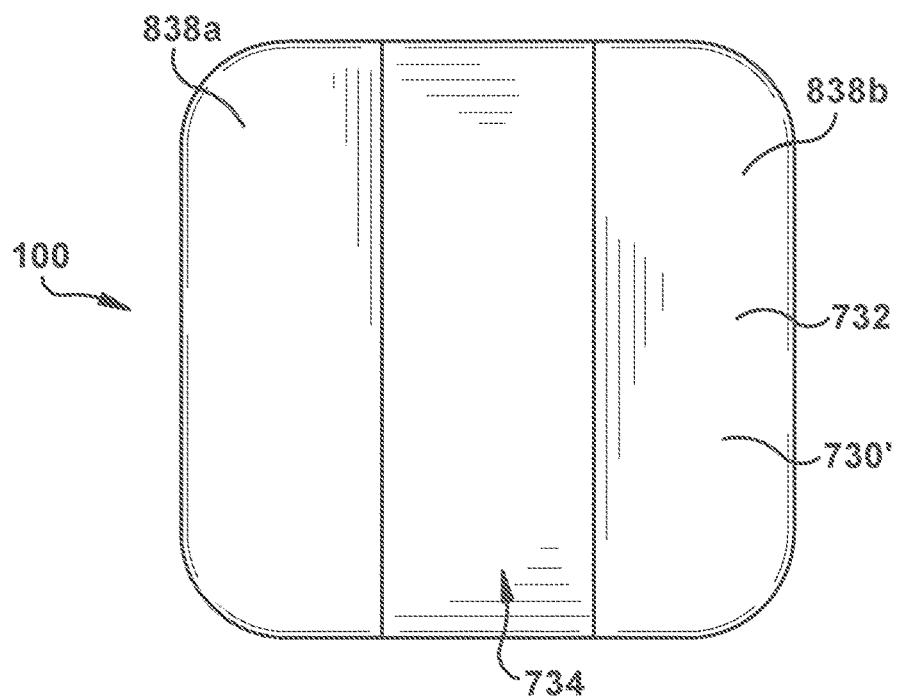
FIG. 8 is a bottom view of the element of FIG. 7.
Figure 9:
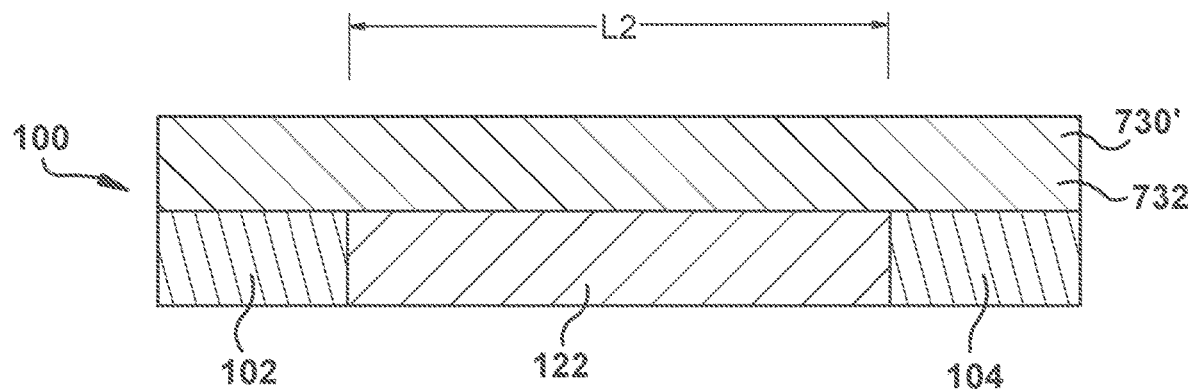
FIG. 9 is a cross-sectional view of an element of FIG. 7.

FIGS. 7-9 depict the triggering element 730 (shown here as the triggering element 730') being formed from one removable portion 732. The triggering element 730' has a first surface 734 and an oppositely facing second surface 736. As shown in FIG. 8, the first surface 734 of the triggering element 730' might include at least two longitudinally spaced triggering element attachment members 838 (shown here as triggering element attachment members 838a, 838b). As shown in FIGS. 7-9, each of the triggering element attachment members 838a, 838b removably attaches the first surface 734 of the triggering element 730' to at least one of the second surface 110 of the first substrate 102, the second surface 112 of the second substrate 104, and the second surface 126 of the elastic spacer 122. As shown in FIG. 9, the triggering element 730', when present, selectively maintains the elastic spacer 122 at a length longer than the first elastic spacer length L1, such as the second elastic spacer length L2, and selectively prevents the elastic spacer 122 from moving toward and achieving the first elastic spacer length L1.

In use of the dressing 100 having the triggering element 730', a target patient site T is located. The target patient site T might be a location on a patient that is desirable to apply a predetermined amount of pressure to the patient's skin, to a wound, to close a wound, to keep a wound closed, to remove tension from a wound, to redistribute tension away from a wound, and/or for any other purpose, though a wound closure use environment is provided here as an example. The elastic spacer 122 is adjusted from the first elastic spacer length L1 to the second elastic spacer length L2. The triggering element 730 formed from one removable portion 732 is attached to at least one of the second surface 110 of the first substrate 102, the second surface 112 of the second substrate 104, and the second surface 126 of the elastic spacer 122 to selectively maintain the elastic spacer 122 at the second elastic spacer length L2 and, with the triggering element 730', selectively prevent the elastic spacer 122 from achieving the first elastic spacer length L1. The process of adjusting the elastic spacer 122 from the first elastic spacer length L1 to the second elastic spacer length L2 and attaching the triggering element 730' to at least one the second surface 110 of the first substrate 102, the second surface 112 of the second substrate 104, and the second surface 126 of the elastic spacer 122 might be completed prior to use, or during use of the dressing 100.

Figure 10:
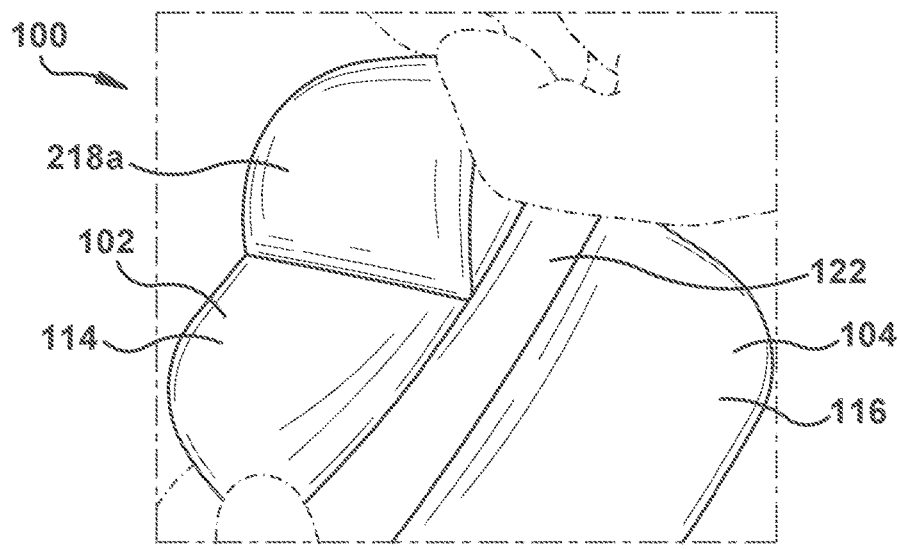
FIGS. 10-14 illustrate an example sequence of operation of a portion of the aspect of FIG. 1, including an element in a first example configuration.
Figure 11:
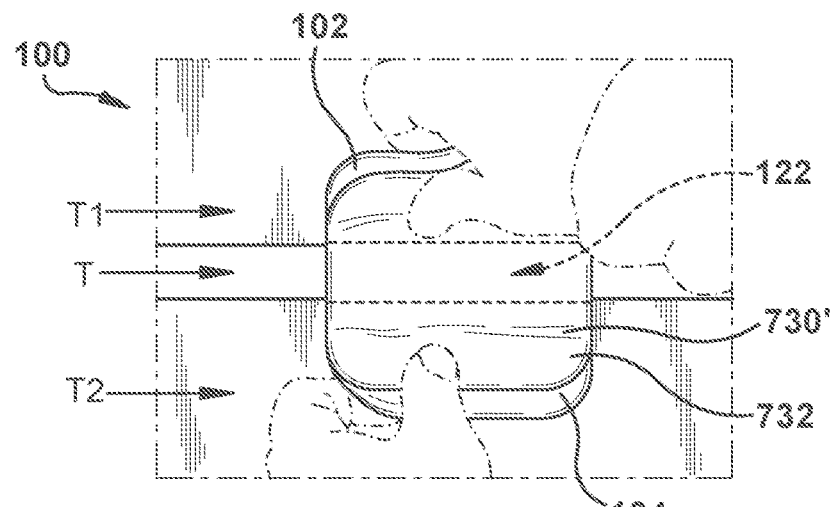
Figure 12:
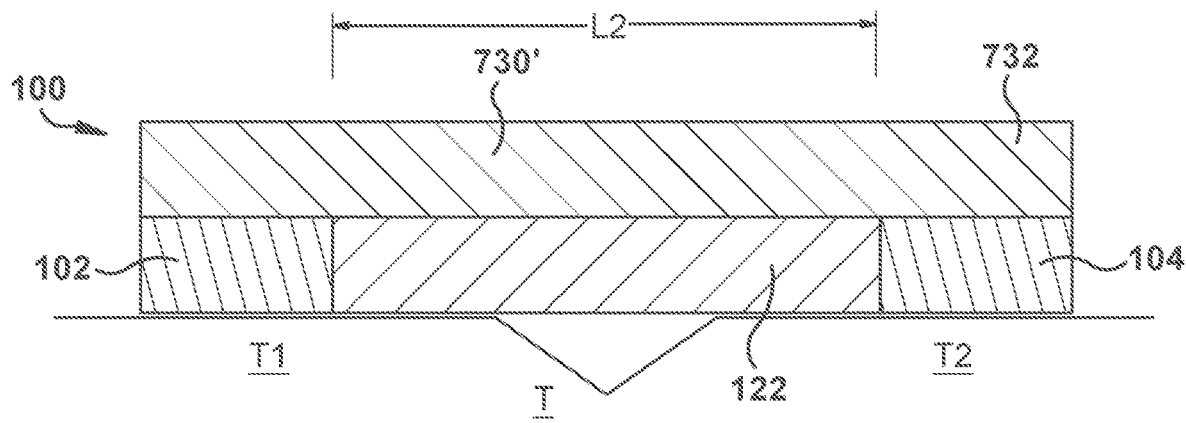

As shown in FIG. 10, each removable cover 218, 220, when present, that is at least partially covering an attachment member 114, 116 of the first and second substrates 102, 104 may be removed from the first and second substrates 102, 104. As shown in FIGS. 11-12, the first substrate 102 is attached to a first side T1 of the patient target site T. The second substrate 104 is attached to a second side T2 of the patient target site T opposite the first side T1, to longitudinally span the patient target site T with the elastic spacer 122.

Figure 13:
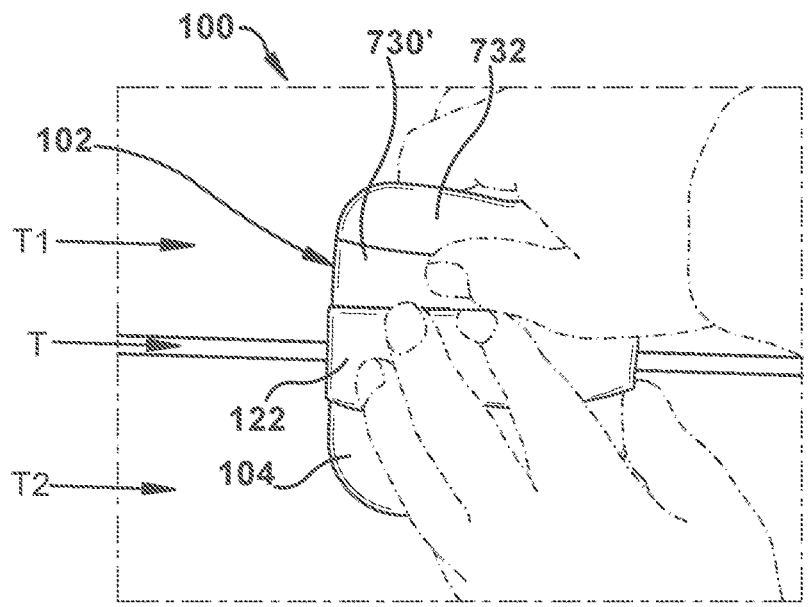
Figure 14:
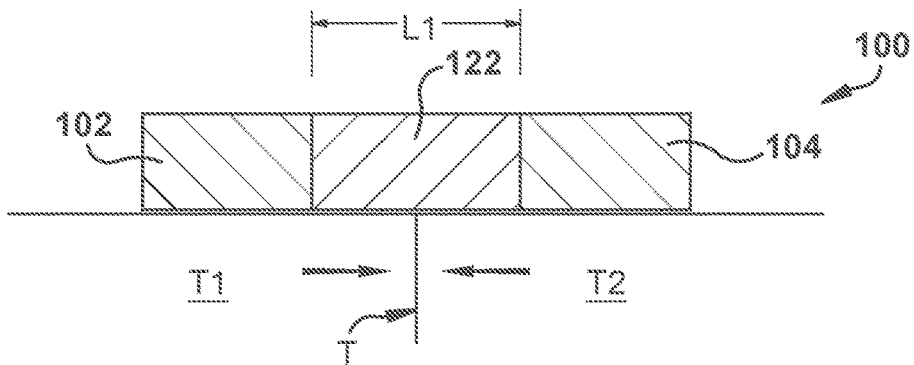

As shown in FIG. 13, the triggering element 730' may be removed. As shown in FIG. 14, the removal of the triggering element 730' causes the elastic spacer 122 to move from the second elastic spacer length L2 to the first elastic spacer length L1. When the at least two interfacing elements 228a, 228b, 228c are present, each of the at least two interfacing elements 228a, 228b, 228c is responsively urged longitudinally toward another when the elastic spacer 122 moves from the second elastic spacer length L2 toward the first elastic spacer length L1, as discussed above.

The movement of the elastic spacer 122 from the second elastic spacer length L2 toward the first elastic spacer length L1 responsively urges the first and second substrates 102, 104 longitudinally toward one another to apply a predetermined amount of longitudinal force to the patient target site T. In particular, the urging of the first and second substrates 102, 104 longitudinally toward one another responsively urges the first and the second sides T1, T2 of the target patient site T longitudinally toward one another to apply a predetermined amount of longitudinal force to the patient target site T. If the first and second sides T1, T2 are on opposing sides of an open wound, the responsive urging of the first and the second sides T1, T2 longitudinally toward one another might at least partially close the wound. T1 and T2 might already be in contact with each other when the dressing 100 is applied. In such case, the responsive urging of the first and second sides T1, T2 longitudinally toward one another further compresses the target patient site T, such as a target patient site T containing a wound, to allow the target patient site T to evert and/or to redistribute tension away from the target patient site T.

FIGS. 15-24 depict the triggering element 730 (shown here as triggering element 730") as being formed from at least two removable portions 732 (shown here as removable portions 732a, 732b, 732c). Each of the at least two removable portions 732a, 732b, 732c might be removably attached to at least one of another removable portion 732a, 732b, 732c, the second surface 110 of the first substrate 102, the second surface 112 of the second substrate 104, and the second surface 126 of the elastic spacer 122, or any combination thereof. The removable attachment might be an adhesive attachment, a magnetic attachment, a hook and loop attachment, a button attachment, any other appropriate attachment, or any combination thereof.

The sequence of operation of the dressing 100 having the trigging element 730" formed from the at least two removable portions 732a, 732b, 732c is substantially similar to the sequence of operation depicted in FIGS. 10-14, and thus the sequence of operation of the dressing 100 having the trigging element 730" formed from the at least two removable portions 732a, 732b, 732c is omitted, for brevity. The main difference between the sequence of operation of the dressing 100 having the trigging element 730" formed from the at least two removable portions 732a, 732b, 732c and the sequence of operation depicted in FIGS. 10-14 is that the at least two removable portions 732a, 732b, 732c of the triggering element 730" are sequentially removable from at least one of another of the at least two removable portions 732a, 732b, 732c, the second surface 110 of the first substrate 102, the second surface 112 of the second substrate 104, and the second surface 126 of the elastic spacer 122 such that as each of the at least two removable portions 732a, 732b, 732c of the triggering element 730 is removed, the elastic spacer 122 sequentially moves from the second elastic spacer length L2 toward the first elastic spacer length L1.

The sequential movement of the elastic spacer 122 from the second elastic spacer length L2 toward the first elastic spacer length L1 responsively urges the first and second substrates 102, 104 longitudinally toward one another to apply a predetermined amount of longitudinal force to the patient target site T. In particular, the urging of the first and second substrates 102, 104 longitudinally toward one another responsively urges the first and the second sides T1, T2 of the target patient site T longitudinally toward one another to apply a predetermined amount of longitudinal force to the patient target site T. Because the movement of the elastic spacer 122 from the second elastic spacer length L2 to the first elastic spacer length L1 is sequential, the amount of longitudinal force applied to the target patient site T sequentially increases. Thus, a user can apply a predetermined amount of longitudinal force to the target patient site T by removing one of the at least two removable portions 732a, 732b, 732c, and increase the amount of longitudinal force by removing another of the at least two removable portions 732a, 732b, 732c.

As shown in FIGS. 15-17 and 18-20, one removable portion, referred to here as a first removable portion 732a, of the at least two removable portions 732a, 732b, 732c might be utilized to selectively maintain another removable portion, referred to here as a second removable portion 732b, of the at least two removable portions 732a, 732b, 732c at a second removable portion length P2. The second removable portion 732b may be biased to a first removable portion length P1 that is shorter than the second removable portion length P2. Removal of the first removable portion 732a responsively urges the second removable portion 732b to move from the second removable portion length P2 to the first removable portion length P1. Movement of the second removable portion 732b from the second removable portion length P2 to the first removable portion length P1 responsively urges the elastic spacer 122 to move from the second elastic spacer length L2 to an intermediate elastic spacer length L3 that is shorter than the second elastic spacer length L2 and longer than the first elastic spacer length L1. Removal of the second removable portion 732b responsively urges the elastic spacer 122 to move from the intermediate elastic spacer length L3 to the first elastic spacer length L1. Thus, the elastic spacer 122 is sequentially moved from the second elastic spacer length L2 to the first elastic spacer length L1.

Figure 15:
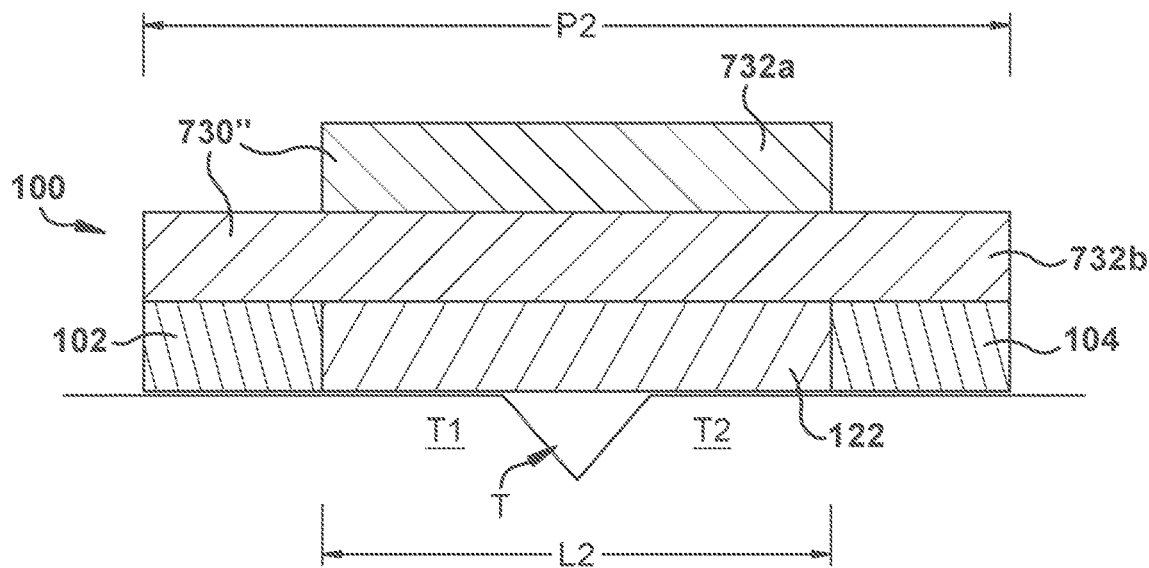
FIGS. 15-17 illustrate an example sequence of operation of a portion of the aspect of FIG. 1, including an element in a second example configuration.
Figure 16:
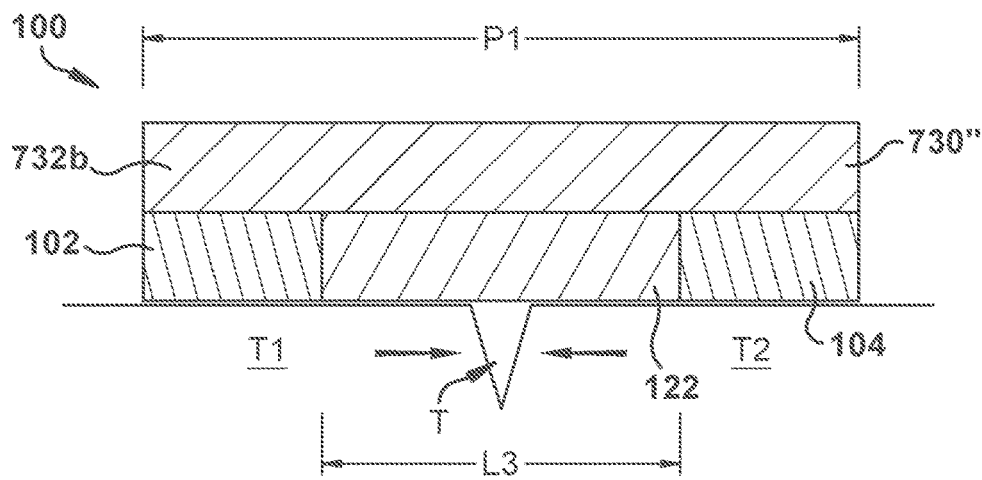
Figure 17:
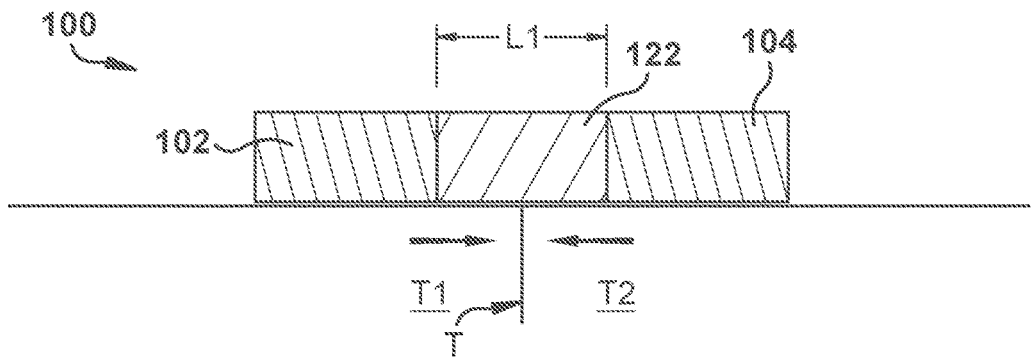

As shown in FIG. 15, the second removable portion 732b might extend from the first substrate 102 to the second substrate 104. In this configuration, the second removable portion length P2 of the second removable portion 732b might be greater than the second elastic spacer length L2. The second removable portion 732b might thus be removably attached to the first substrate 102, the elastic spacer 122, and the second substrate 104. The first removable portion 732a might have a length that is less than the second removable portion length P2 of the second removable portion 732b so that the first removable portion 732a might only be attached to the second removable portion 732b.

Figure 18:
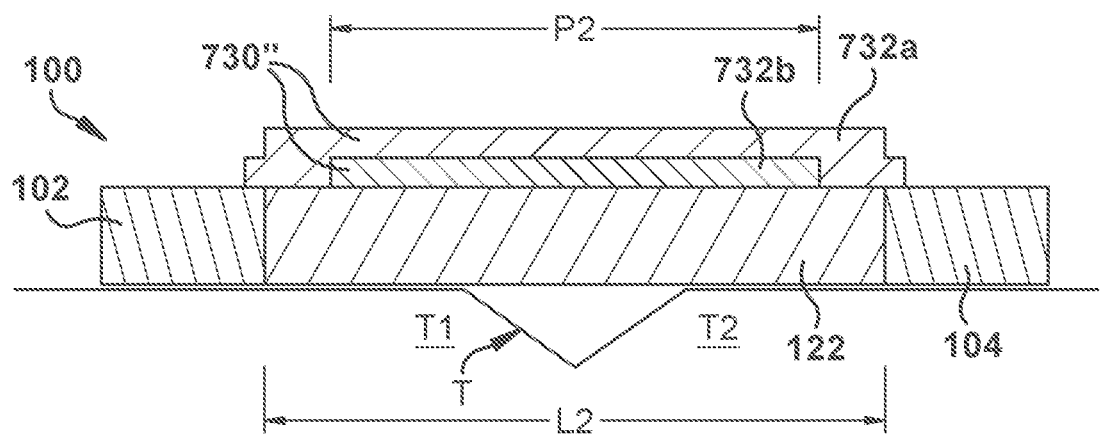
FIGS. 18-20 illustrate an example sequence of operation of a portion of the aspect of FIG. 1, including an element in a third example configuration.
Figure 19:
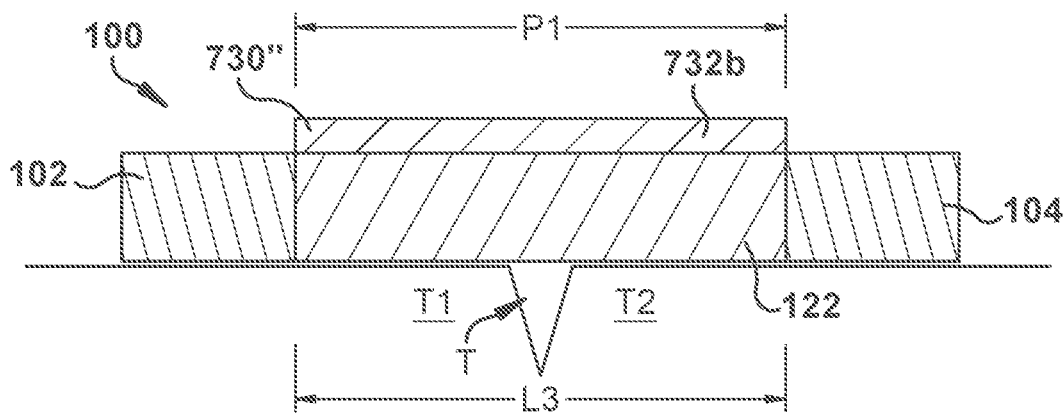
Figure 20:
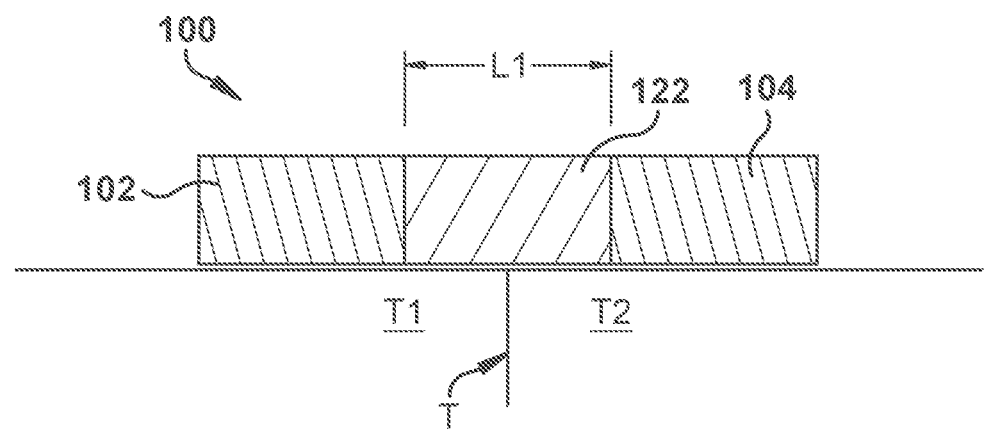
Figure 21:
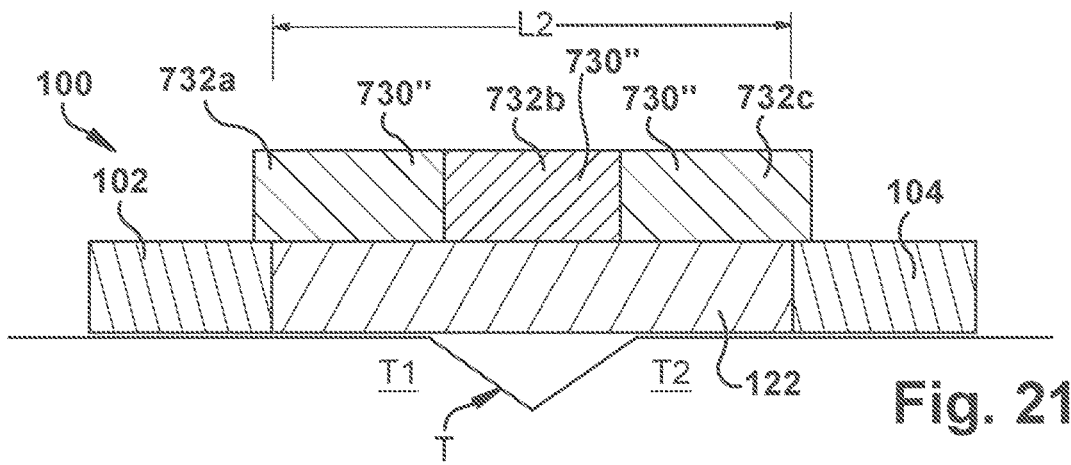
FIGS. 21-24 illustrate an example sequence of operation of a portion of the aspect of FIG. 1, including an element in a fourth example configuration.
Figure 22:
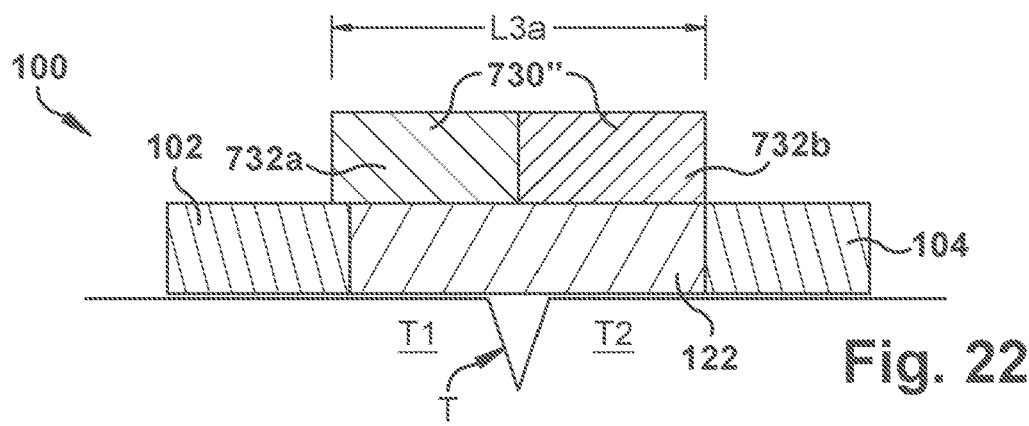
Figure 23:
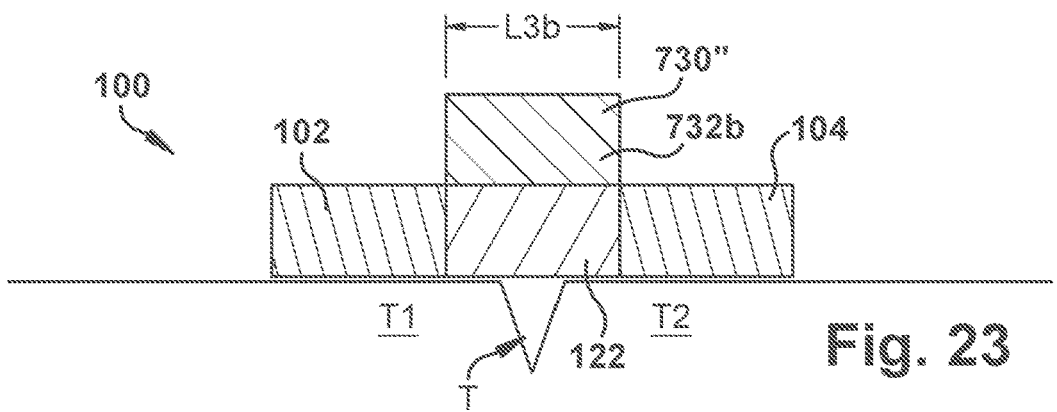
Figure 24:
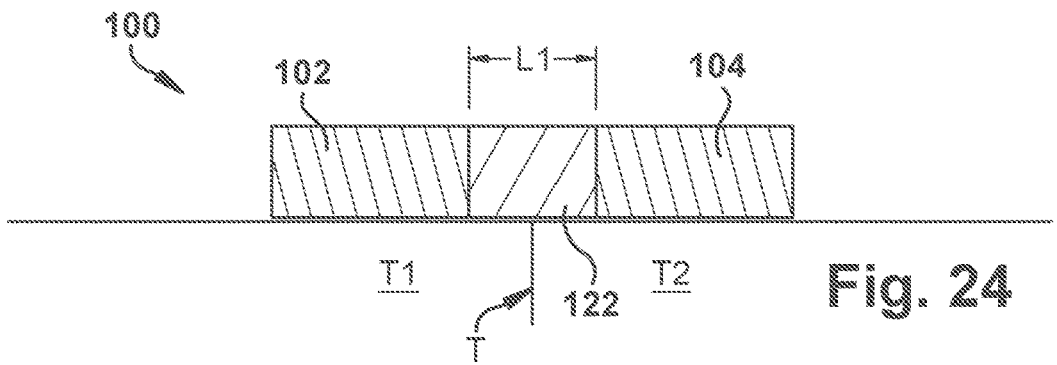

As shown in FIG. 18, the second removable portion length P2 of the second removable portion 732b might be less than the second elastic spacer length L2 of the elastic spacer 122. In this configuration, the second removable portion 732b might be removably attached only to the elastic spacer 122. The first removable portion 732a, however, might have a length that is greater than the second removable portion length P2 so that the first removable portion 732a might be removably attached to the first substrate 102, the second removable portion 732b, and the second substrate 104. At least one portion of the first removable portion 732a might also be attached to the elastic section 122. Further, the first removable portion 732a might partially encompass the second removable portion 732b by surrounding at least three sides of the second removable portion 732b.

As shown in FIGS. 21-24, a chosen one of the at least two removable portions 732a, 732b, 732c might be longitudinally parallel to another of the at least two removable portions 732a, 732b, 732c. Similar to the above, as each of the at least two removable portions 732a, 732b, 732c are removed, the elastic spacer 122 moves from the second elastic spacer length L2 to the first elastic spacer length L1 sequentially by moving to at least one intermediate elastic spacer length L3 (shown here as L3a, L3b) before moving to the first elastic spacer length L1.

Figure 25:
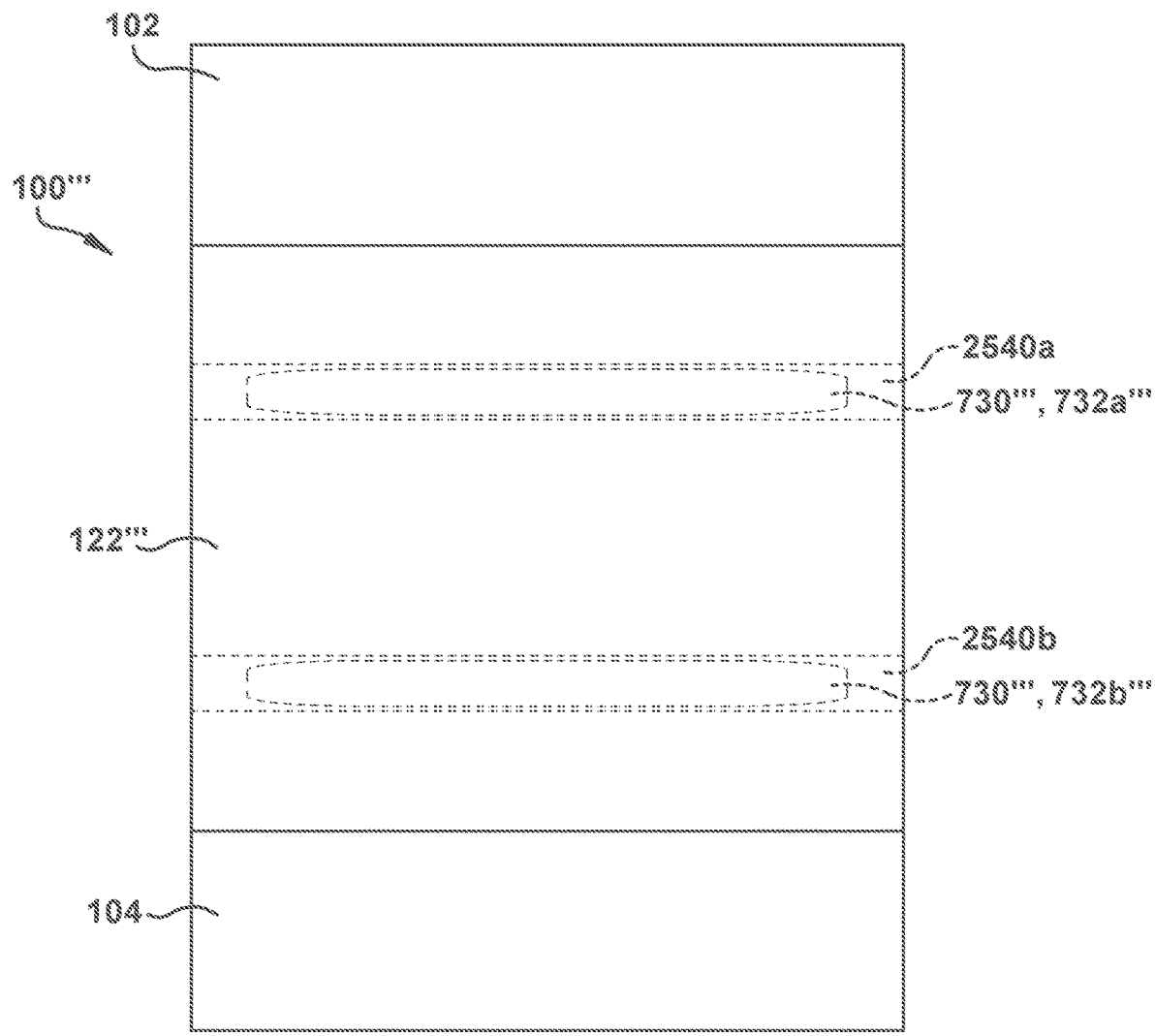
FIG. 25 is a top view of the aspect of FIG. 1, in a second example configuration.

FIG. 25 shows another configuration for the dressing 100''', which may differ from that shown in FIGS. 1-24. Therefore, structures of FIG. 25 that are the same as or similar to those described with reference to FIGS. 1-25 are either unnumbered or have the same reference numbers with the addition of a "triple prime" mark. Description of common elements and operation similar to those in the previously described configuration will not be repeated with respect to the configuration of FIG. 25, for brevity.

Figure 26:
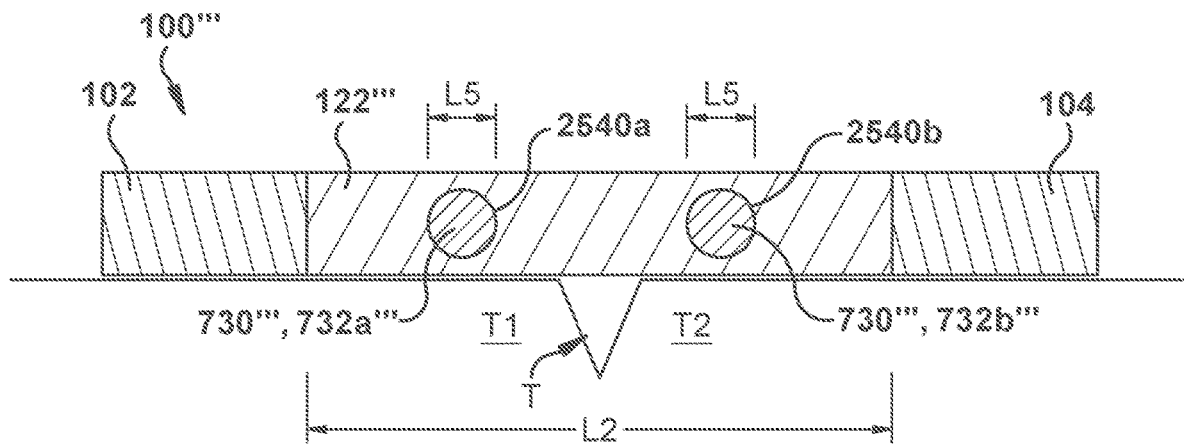
FIGS. 26-28 illustrate an example sequence of operation of a portion of the aspect of FIG. 25.

In the example configuration of FIG. 25, the elastic spacer 122''' includes at least one expandable cavity 2540 (shown here as expandable cavities 2540a, 2540b) that laterally extends at least partially through the elastic spacer 122'''. The term "lateral" is used herein to indicate a direction substantially perpendicular to the "longitudinal" direction, and is shown as the horizontal direction in the orientation of FIG. 25. The at least one expandable cavity 2540a, 2540b may be biased to a closed configuration in which the at least one expandable cavity 2540a, 2540b has a first cavity length L4 (FIG. 28), which is measured in the longitudinal direction. The at least one expandable cavity 2540a, 2540b is configured to be selectively moved between the closed configuration and an opened configuration. The at least one expandable cavity 2540a, 2540b in the opened configuration has a second cavity length L5, which is measured in the longitudinal direction and longer than the first cavity length L4 (FIG. 26).

Figure 27:
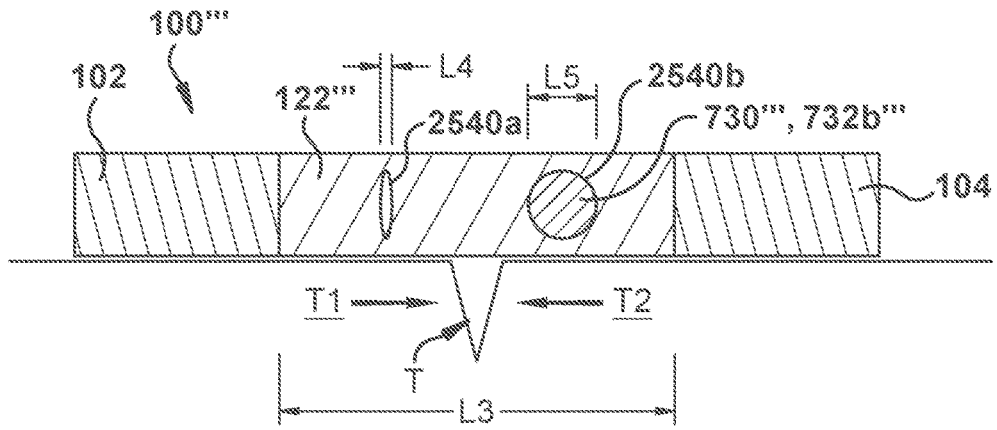
Figure 28:
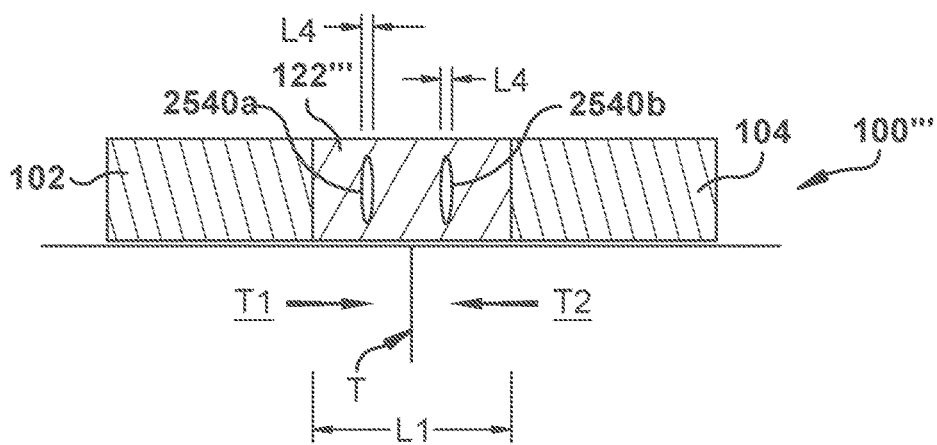

When each expandable cavity 2540a, 2540b of the elastic spacer 122''' is in the closed configuration, the elastic spacer 122''' is biased to the first elastic spacer length L1 (FIG. 28). The elastic spacer 122''' may be selectively moved from the first elastic spacer length L1 to the second elastic spacer length L2 by selectively moving each expandable cavity 2540a, 2540b of the elastic spacer 122''' to the opened configuration (FIG. 26). The elastic spacer 122''' might be configured to be selectively moved to the intermediate elastic spacer length L3 by selectively moving at least one expandable cavity 2540a, 2540b to the opened configuration while at least one other expandable cavity 2540a, 2540b is selectively moved to the closed configuration (FIG. 27).

To selectively maintain the at least one expandable cavity 2540a, 2540b in the opened configuration, the dressing 100''' may include a triggering element 730''' formed from at least one removable portion 732''' (shown here as removable portions 732a''', 732b''') that is removably inserted into the at least one expandable cavity 2540a, 2540b. The at least one removable portion 732a''', 732b''' might be in the form of a rigid bar or rod, though the at least one removable portion 732a''', 732b''' might have any desired form corresponding to the shape of the at least one expandable cavity 2540a, 2540b. The at least one removable portion 732a''', 732b''' has a longitudinal length that is about equal to the second cavity length L5. Thus, when the at least one removable portion 732a''', 732b''' is selectively inserted into the at least one expandable cavity 2540a, 2540b, the at least one expandable cavity 2540a, 2540b is maintained in the opened configuration. The at least one removable portion 732a''', 732b''' might have a lateral length, that is greater than, equal to, or less than the lateral length of the at least one expandable cavity 2540a, 2540b.

In use of the dressing 100''' having the triggering element 730''', a target patient site T is located. The elastic spacer 122''' is adjusted from the first elastic spacer length L1 to the second elastic spacer length L2. The triggering element 730''' formed from the at least one removable portion 732a''', 732b''' is inserted into the at least one expandable cavity 2540a, 2540b of the elastic spacer 122''' to selectively maintain the elastic spacer 122''' at the second elastic spacer length L2 and, with the triggering element 730''', selectively prevent the elastic spacer 122''' from achieving the first elastic spacer length L1. The process of adjusting the elastic spacer 122''' from the first elastic spacer length L1 to the second elastic spacer length L2 and inserting the triggering element 730''' into the at least one expandable cavity 2540a, 2540b of the elastic spacer 122''' might be completed prior to use, or during use of the dressing 100'''.

Each removable cover 218, 220, when present, that is at least partially covering an attachment member 114, 116 of the first and second substrates 102, 104 may be removed from the first and second substrates 102, 104. As shown in FIG. 26, the first substrate 102 is attached to a first side T1 of the patient target site T. The second substrate 104 is attached to a second side T2 of the patient target site T opposite the first side T1, to longitudinally span the patient target site T with the elastic spacer 122'''.

With the first and second substrates 102, 104 attached to the first and second sides T1, T2 of the target patient tissue site T, the at least one removable portion 732a''', 732b''' of the triggering element 730''' may be selectively laterally removed from the at least one expandable cavity 2540a, 2540b. The removal of the at least one removable portion 732a''', 732b''' causes the elastic spacer 122''' to move from the second elastic spacer length L2 to the first elastic spacer length L1. The movement of the elastic spacer 122''' from the second elastic spacer length L2 toward the first elastic spacer length L1 responsively urges the first and second substrates 102, 104 longitudinally toward one another to apply a predetermined amount of longitudinal force to the patient target site T. In particular, the urging of the first and second substrates 102, 104 longitudinally toward one another responsively urges the first and the second sides T1, T2 of the target patient site T longitudinally toward one another to apply a predetermined amount of longitudinal force to the patient target site T.

As shown in FIGS. 26-28, the triggering element 730''' might include more than one removable portion 732a''', 732b'''. In the example configuration shown in FIGS. 26-28, the triggering element 730''' of the dressing 100''' includes at least two removable portions 732a''', 732b'''. The at least two removable portions 732a''', 732b''' of the triggering element 730''' are sequentially laterally removable from corresponding expandable cavities 2540a, 2540b of the elastic spacer 122'' such that as each of the at least two removable portions 732a''', 732b''' of the triggering element 730''' is removed, the elastic spacer 122''' sequentially moves from the second elastic spacer length L2 toward the first elastic spacer length L1.

The sequential movement of the elastic spacer 122''' from the second elastic spacer length L2 toward the first elastic spacer length L1 responsively urges the first and second substrates 102, 104 longitudinally toward one another to apply a predetermined amount of longitudinal force to the patient target site T. In particular, the urging of the first and second substrates 102, 104 longitudinally toward one another responsively urges the first and the second sides T1, T2 of the target patient site T longitudinally toward one another to apply a predetermined amount of longitudinal force to the patient target site T. Because the movement of the elastic spacer 122''' from the second elastic spacer length L2 to the first elastic spacer length L1 is sequential, the amount of longitudinal force applied to the target patient site T sequentially increases. Thus, a user can apply a predetermined amount of longitudinal force to the target patient site T by laterally removing one of the at least two removable portions 732a''', 732b''', and increase the amount of longitudinal force by laterally removing another of the at least two removable portions 732a''', 732b'''.

As shown in FIGS. 26-27, lateral removal of a first removable portion 732a responsively urges a corresponding first expandable cavity 2540a to the closed configuration from the opened configuration. The first expandable cavity 2540a moving to the closed configuration responsively urges the elastic spacer 122''' to move from the second elastic spacer length L2 to the intermediate elastic spacer length L3 that is shorter than the second elastic spacer length L2 and longer than the first elastic spacer length L1. As shown in FIGS. 27-28, removal of a second removable portion 732b''' responsively urges a corresponding second expandable cavity 2540b to the closed configuration from the opened configuration. The second expandable cavity 2540b moving to the closed configuration responsively urges the elastic spacer 122''' to move from the intermediate elastic spacer length L3 to the first elastic spacer length L1. Thus, the elastic spacer 122''' is sequentially moved from the second elastic spacer length L2 to the first elastic spacer length L1.

Although certain features shown in FIGS. 25-28 have been shown only in regard to the hand support and assist device 100''', one of ordinary skill in the art will understand that any of these features may be incorporated in any other configuration, discussed or not, of the dressing 100, 100'''. Further, any other feature described above with respect to a particular configuration might be incorporated into any other configuration, discussed or not, of the dressing 100, 100'''. Additionally, although some of the Figures do not depict certain features depicted in other Figures, each feature of the dressing 100, 100''' might be present in any of the Figures whether expressly shown or not.

It is contemplated that the dressing 100, 100''' might be applied to certain medical instruments that are on opposing sides of a target patient site T so that the dressing 100, 100''' is able to apply pressure, i.e., a longitudinal force, to the target site T through the medical instruments.

It is contemplated that the dressing 100, 100''' might have other applications unrelated to a patient and/or a target patient site. For example, the dressing 100, 100''' might be used in any situation that is desirable to apply pressure, i.e., a longitudinal force, to a site by urging two opposing sides toward one another.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

I claim:

1. A dressing for applying pressure to a patient target site, comprising:
   longitudinally spaced first and second substrates each having a first surface and an oppositely facing second surface, the first surface of each of the first and the second substrates having an attachment member for attaching the dressing to the patient target site;
   an elastic spacer longitudinally extending between the first and the second substrates, the elastic spacer being biased to a first length, the elastic spacer being configured to be selectively moved between the first length and a second length, the second length being longer than the first length; and
   a triggering element laterally removably inserted into a corresponding expandable cavity of the elastic spacer, the triggering element, when present, selectively maintaining the elastic spacer at the second length and selectively preventing the elastic spacer from moving toward the first length, the triggering element being removable from the corresponding expandable cavity of the elastic spacer such that as the triggering element is removed, the elastic spacer moves from the second length toward the first length, wherein the triggering element is formed from at least two removable portions, each of the at least two removable portions being laterally removably inserted into a corresponding expandable cavity of the elastic spacer; and wherein the elastic spacer has a first surface and an oppositely facing second surface, the first surface being configured to face toward the patient target site, and the expandable cavity being located between the first and second surfaces of the elastic spacer.

2. The dressing of claim 1, wherein the elastic spacer has a first surface and an oppositely facing second surface, the first surface of the elastic spacer having at least one interfacing element for contacting the patient target site.

3. The dressing of claim 2, wherein the at least one interfacing element is at least one of gauze, perforated plastic film dressing, and alginate.

4. The dressing of claim 2, wherein when the elastic spacer is biased to the first length, the at least one interfacing element continuously spans between the first and second substrates.

5. The dressing of claim 2, wherein the at least one interfacing element is at least two interfacing elements, a chosen one of the at least two interfacing elements being longitudinally parallel with another of the at least two interfacing elements, the at least two interfacing elements being longitudinally spaced apart from one another when the elastic spacer is moved to the second length, the chosen one of the at least two interfacing elements directly longitudinally contacting another of the at least two interfacing elements when the elastic spacer is biased to the first length so that the at least two interfacing elements, as a whole, continuously span between the first and second substrates.

6. The dressing of claim 1, wherein the at least two removable portions of the triggering element are sequentially removable from the corresponding expandable cavities such that as each of the at least two removable portions of the triggering element is removed, the elastic spacer sequentially moves from the second length toward the first length.

7. The dressing of claim 6, wherein as the elastic spacer sequentially moves from the second length toward the first length, an amount of longitudinal force applied to the target patient target site sequentially increases.

8. The dressing of claim 1, wherein the triggering element, when inserted into the corresponding expandable cavity, is located between the first and second surfaces of the elastic spacer.

9. The dressing of claim 8, wherein the first and second surfaces of the elastic spacer are spaced from one another in a transverse direction, an entire transverse height of the triggering element being located between the first and second surfaces of the elastic spacer when the triggering element is inserted into the corresponding expandable cavity.

10. The dressing of claim 1, including at least one removable cover at least partially covering each of the attachment members of the first and second substrates.

11. The dressing of claim 1, wherein the expandable cavity is spaced from each of the first and second surfaces of the elastic spacer.

12. The dressing of claim 1, wherein the triggering element, when inserted into the corresponding expandable cavity, is spaced from each of the first and second surfaces of the elastic spacer.

* * * * *